United States Patent [19]

Unger

[11] Patent Number: 5,209,720
[45] Date of Patent: * May 11, 1993

[54] METHODS FOR PROVIDING LOCALIZED THERAPEUTIC HEAT TO BIOLOGICAL TISSUES AND FLUIDS USING GAS FILLED LIPOSOMES

[76] Inventor: Evan C. Unger, 13365 E. Camino La Cebadilla, Tucson, Ariz. 85749

[*] Notice: The portion of the term of this patent subsequent to Sep. 22, 2009 has been disclaimed.

[21] Appl. No.: 716,793

[22] Filed: Jun. 18, 1991

Related U.S. Application Data

[63] Continuation-in-part of Ser. No. 581,027, Sep. 11, 1990, and a continuation-in-part of Ser. No. 569,828, Aug. 20, 1990, Pat. No. 5,088,499, which is a continuation-in-part of Ser. No. 455,707, Dec. 22, 1989, abandoned.

[51] Int. Cl.$^5$ .............................................. A61B 17/20
[52] U.S. Cl. .................................. 604/22; 128/24 AA; 128/24 R; 128/660.03; 128/662.02; 604/19; 424/5; 424/9
[58] Field of Search .......................... 264/4.2, 4.1, 4.6; 424/9, 44, 43, 450; 436/829; 128/24 EL, 24 AA, 24 R, 660.01-660.07, 653; 600/10, 12; 604/22, 20

[56] References Cited

U.S. PATENT DOCUMENTS

| | | | |
|---|---|---|---|
| 4,162,282 | 7/1979 | Fulwyler et al. | 264/9 |
| 4,310,505 | 1/1982 | Baldeschwieler et al. | 424/1 |
| 4,533,254 | 8/1985 | Cook et al. | 366/176 |
| 4,586,512 | 5/1986 | Do-huu et al. | 128/660 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,689,986 | 9/1987 | Carson et al. | 73/19 |
| 4,728,575 | 3/1988 | Gamble et al. | 428/402.2 |
| 4,728,578 | 3/1988 | Higgins et al. | 428/462 |
| 4,737,323 | 4/1988 | Martin et al. | 264/4.3 |
| 4,865,836 | 9/1989 | Long, Jr. | 424/5 |
| 4,893,624 | 1/1990 | Lele | 128/399 |
| 4,900,540 | 2/1990 | Ryan et al. | 424/9 |
| 4,921,706 | 5/1990 | Roberts et al. | 424/450 |
| 5,088,499 | 2/1992 | Unger | 128/662.02 |

FOREIGN PATENT DOCUMENTS

US80/00502 5/1980 PCT Int'l Appl. .
US81/01526 11/1981 PCT Int'l Appl. .

OTHER PUBLICATIONS

Ostro, Marc ed. *Liposomes:* pp. 38-39; Marcel Dekker, New York, 1983.
Cheng et al, *Investigative Radiology*, vol. 22, pp. 47-55 (1987).
Crowe et al., *Archives of Biochemistry and Biophysics*, vol. 242, pp. 240-247 (1985).
Crowe et al., *Archives of Biochemistry and Biophysics*, vol. 220, pp. 477-484 (1983).
Dorland's Illustrated Medical Dictionary, p. 946, 27th ed. (W. B. Saunders Company, Philadelphia 1988).

(List continued on next page.)

*Primary Examiner*—C. Fred Rosenbaum
*Assistant Examiner*—Chalin Smith
*Attorney, Agent, or Firm*—Woodcock Washburn Kurtz Mackiewicz & Norris

[57] ABSTRACT

Gas filled liposomes prepared by a vacuum drying gas instillation method and/or gas filled liposomes substantially devoid of liquid in the interior thereof, are presented as novel potentiators for ultrasonic hyperthermia. The liposomes of the present invention, which may be administered into the vasculature, interstitially or into any body cavity are designed to accumulate in cancerous and diseased tissues. When therapeutic ultrasonic energy is applied to the diseased region heating is increased because of the greater effectiveness of sound energy absorption caused by these agents.

16 Claims, 2 Drawing Sheets

OTHER PUBLICATIONS

Fukuda et al., *J. Am. Chem. Soc.*, vol. 108, pp. 2321–2327 (1986).
Hope et al., *Biochimica et Biophysica Acta*, vol. 812, pp. 55–65 (1985).
*Liposomes Technology*, Gregoriadis, G., ed., vol. I, pp. 1–18, 29–37, 51–67 and 79–108 (CRC Press Inc., Boca Raton, Fla., 1984).
Madden et al., *Chemistry and Physics of Lipids*, vol. 53, pp. 37–46 (1990).
Mayer et al., *Biochimica et Biophysica Acta*, vol. 858, pp. 161–168 (1986).
Mayhew et al., *Methods in Enzymology*, vol. 149, pp. 64–77 (1987).
Regen et al., *J. Am. Chem. Soc.*, vol. 102, pp. 6638–6640 (1980).
Sinkula et al., *J. Pharm. Sci.*, vol. 64, pp. 181–210 (1975).
Shiina et al., "Hyperthermiaby Low-frequency Synthesized Ultrasound", *IEEE Engineering*, pp. 879–880, vol. 2 (abstract).
McAvoy et al., *IEEE Engineering, Ultrasonics Symposium Proceedings*, vol. 2, pp. 677–1248 (abstract).

METHODS FOR PROVIDING LOCALIZED THERAPEUTIC HEAT TO BIOLOGICAL TISSUES AND FLUIDS USING GAS FILLED LIPOSOMES

RELATED APPLICATION

This application is a continuation-in-part of copending application U.S. Ser. No. 581,027, filed Sep. 11, 1990 now allowed and a continuation-in-part of copending application U.S. Ser. No. 569,828, filed Aug. 20, 1990 now U.S. Pat. No. 5,088,499 which in turn is a continuation-in-part of application U.S. Ser. No. 455,707, filed Dec. 22, 1989 now abandoned, the disclosures of each of which are hereby incorporated herein by reference in their entirety.

BACKGROUND OF THE INVENTION

1. Field of the Invention

The present invention relates to the use of ultrasonic energy to heat biological tissues and fluids, and more specifically, to the use of hyperthermia potentiators, such as gas filled liposomes prepared by a vacuum drying gas instillation method, and/or gas filled liposomes substantially devoid of liquid in the interior thereof, in combination with ultrasound to facilitate the selective heating of the tissues and fluids.

2. Description of the Prior Art

The usefulness of heat to treat various inflammatory and arthritic conditions has long been known. The use of ultrasound to generate such heat for these as well as other therapeutic purposes, such as in, for example, the treatment of tumors has, however, been a fairly recent development.

Where the treatment of inflammation and arthritis is concerned, the use of the ultrasound induced heat serves to increase blood flow to the affected regions, resulting in various beneficial effects. Moreover, when ultrasonic energy is delivered to a tumor, the temperature of the tumorous tissue rises, generally at a higher rate than in normal tissue. As this temperature reaches above about 43° C., the tumorous cells begin to die and, if all goes well, the tumor eventually disappears. Ultrasound induced heat treatment of biological tissues and fluids is known in the art as hyperthermic ultrasound.

The non-invasive nature of the hyperthermia ultrasound technique is one of its benefits. Nonetheless, in employing hyperthermic ultrasound, certain precautions must be taken. Specifically, one must be careful to focus the ultrasound energy on only the areas to be treated, in an attempt to avoid heat-induced damage to the surrounding, non-targeted, tissues. In the treatment of tumors, for example, when temperatures exceeding about 43° C. are reached, damage to the surrounding normal tissue is of particular concern. This concern with over heating the non-target tissues thus places limits on the use of hyperthermic ultrasound. Such therapeutic treatments would clearly be more effective and more widely employed if a way of targeting the desired tissues and fluids, and of maximizing the heat generated in those targeted tissues, could be devised.

The present invention is directed toward improving the effectiveness and utility of hyperthermic ultrasound by providing agents capable of promoting the selective heating of targeted tissues and body fluids.

SUMMARY OF THE INVENTION

The present invention is directed to methods for heat treating biological tissues and fluids which comprise administering to the tissue or fluid to be treated a therapeutically effective amount of a hyperthermia potentiator comprising gas filled liposomes prepared by a vacuum drying gas instillation method, and then applying ultrasound to that tissue or fluid.

The present invention is also directed to methods for heat treating biological tissues and fluids which comprise administering to the tissue or fluid to be treated a therapeutically effective amount of a hyperthermia potentiator comprising gas filled liposomes substantially devoid of liquid in the interior thereof, and then applying ultrasound to that tissue or fluid.

By using the potentiators of the present invention, hyperthermic ultrasound becomes a better, more selective and more effective therapeutic method for the treatment of tumors, inflammation, and arthritis, as well as other various conditions.

DETAILED DESCRIPTION OF THE INVENTION

Figure 1:
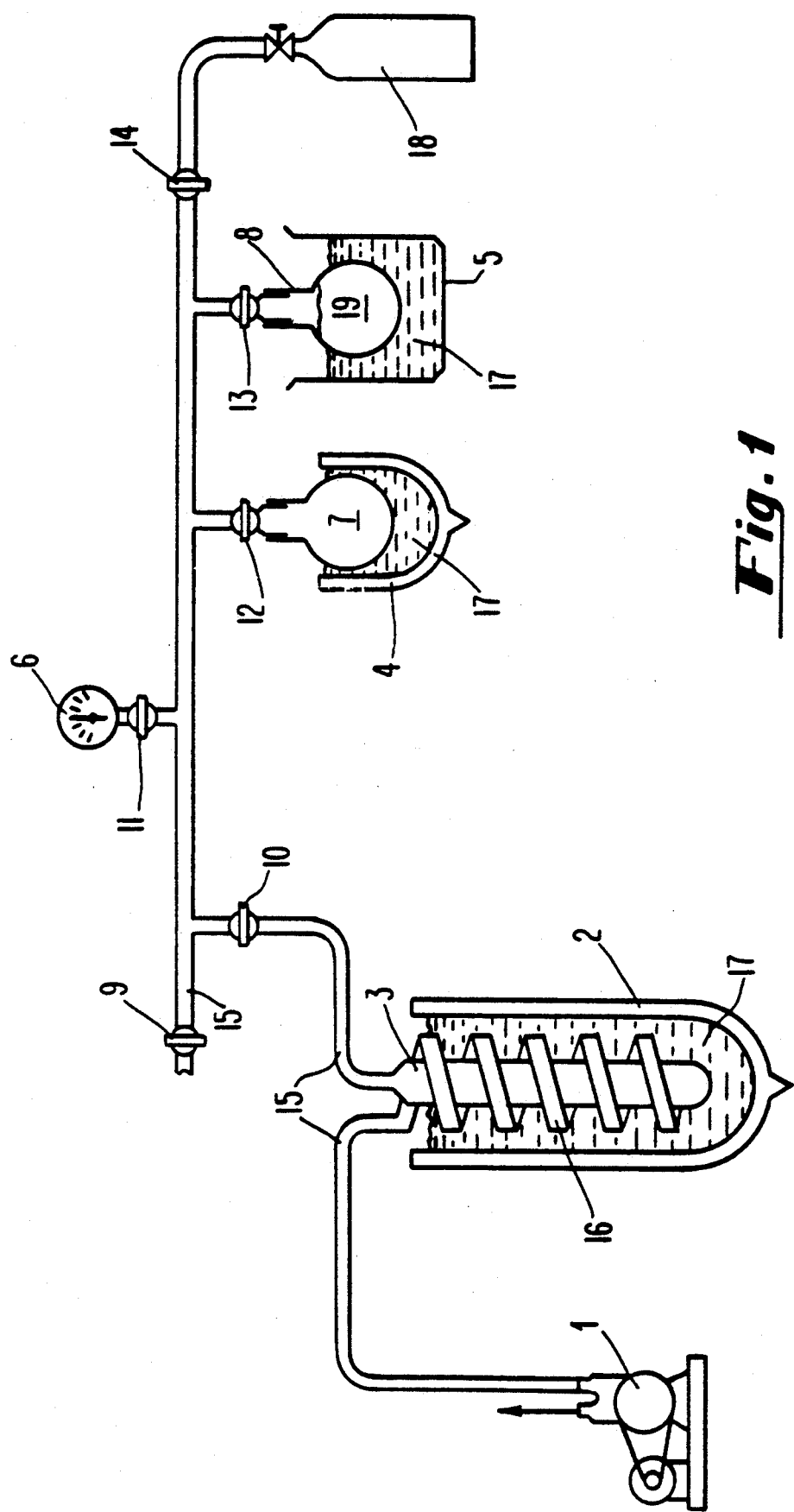
FIG. 1 shows an apparatus according to the present invention for preparing the vacuum dried gas instilled liposomes and the gas filled liposomes substantially devoid of liquid in the interior thereof prepared by the vacuum drying gas instillation method.

The present invention is directed to a method for heat treating biological tissues and fluids comprising administering to the tissue or fluid to be treated a therapeutically effective amount of a hyperthermia potentiator, and then applying ultrasound to said tissue or fluid.

The hyperthermia potentiators described herein comprise gas filled liposomes prepared by a vacuum drying gas instillation method, and/or gas filled liposomes substantially devoid of liquid in the interior thereof.

The vacuum drying gas instillation method, which may be employed to prepare both the gas filled liposomes prepared by the vacuum drying gas instillation method, and the gas filled liposomes substantially devoid of liquid in the interior thereof, contemplates the following process. First, in accordance with the process, the liposomes are placed under negative pressure (that is, reduced pressure or vacuum pressure). Next, the liposomes are incubated under that negative pressure for a time sufficient to remove substantially all liquid from the liposomes, thereby resulting in substantially dried liposomes. By removal of substantially all liquids, and by substantially dried liposomes, as those phrases are used herein, it is meant that the liposomes are at least about 90% devoid of liquid, preferably at least about 95% devoid of liquid, most preferably about 100% devoid of liquid. Finally, the liposomes are instilled with selected gas by applying the gas to the liposomes until ambient pressures are achieved, thus resulting in the subject vacuum dried gas instilled liposomes of the present invention, and the gas filled liposomes of the invention substantially devoid of liquid in the interior thereof. By substantially devoid of liquid in the interior thereof, as used herein, it is meant liposomes having an interior that is at least about 90% devoid of liquid, preferably at least about 95% devoid of liquid, most preferably about 100% devoid of liquid.

Unexpectedly, the liposomes prepared in accordance with the vacuum dried gas instillation method, and the gas filled liposomes substantially devoid of liquid in the interior thereof, possess a number of surprising yet highly beneficial characteristics. The liposomes of the invention exhibit intense ecogenicity on ultrasound, result in good heating of surrounding tissues and/or fluids on ultrasound, are highly stable to pressure, and/or possess a long storage life either when stored dry or suspended in a liquid medium.

The ecogenicity of the liposomes allows the monitoring of the liposomes following administration to a patient to determine the presence of liposomes in a desired region. The ability of the liposomes to result in heating of the surrounding region is of obvious importance to the therapeutic applications of the invention.

The stability of the liposomes is also of great practical importance. The subject liposomes tend to have greater stability during storage than other gas filled liposomes produced via known procedures such as pressurization or other techniques. At 72 hours after formation, for example, conventionally prepared liposomes often are essentially devoid of gas, the gas having diffused out of the liposomes and/or the liposomes having ruptured and/or fused, resulting in a concomitant loss in heating potential. In comparison, gas filled liposomes of the present invention generally have a shelf life stability of greater than about three weeks, preferably a shelf life stability of greater than about four weeks, more preferably a shelf life stability of greater than about five weeks, even more preferably a shelf life stability of greater than about three months, and often a shelf life stability that is even much longer, such as over six months, twelve months or even two years.

Also unexpected is the ability of the liposomes during the vacuum drying gas instillation process to fill with gas and resume their original circular shape, rather than collapse into a cup-shaped structure, as the prior art would cause one to expect. See, e.g., Crowe et al., *Archives of Biochemistry and Biophysics*, Vol. 242, pp. 240-247 (1985); Crowe et al., *Archives of Biochemistry and Biophysics*, Vol. 220, pp. 477-484 (1983); Fukuda et al., *J. Am. Chem. Soc.*, Vol. 108, pp. 2321-2327 (1986); Regen et al., *J. Am. Chem. Soc.*, Vol. 102, pp. 6638-6640 (1980).

The liposomes subjected to the vacuum drying gas instillation method of the invention may be prepared using any one of a variety of conventional liposome preparatory techniques which will be apparent to those skilled in the art. These techniques include freeze-thaw, as well as techniques such as sonication, chelate dialysis, homogenization, solvent infusion, microemulsification, spontaneous formation, solvent vaporization, French pressure cell technique, controlled detergent dialyzing, and others. The size of the liposomes can be adjusted, if desired, prior to vacuum drying and gas instillation, by a variety of procedures including extrusion, filtration, sonication, homogenization, employing a laminar stream of a core of liquid introduced into an immiscible sheath of liquid, and similar methods, in order to modulate resultant liposomal biodistribution and clearance, with extrusion under pressure through pores of defined size being the preferred means of adjusting the size of the liposomes. The foregoing techniques, as well as others, are discussed, for example, in U.S. Pat. No. 4,728,578; U.K. Patent Application GB 2193095 A; U.S. Pat. No. 4,728,575; U.S. Pat. No. 4,737,323; International Application PCT/US85/01161; Mayer et al., *Biochimica et Biophysica Acta*, Vol. 858, pp. 161-168 (1986); Hope et al., *Biochimica et Biophysica Acta*, Vol. 812, pp. 55-65 (1985); U.S. Pat. No. 4,533,254; Mayhew et al., *Methods in Enzymology*, Vol. 149, pp. 64-77 (1987); Mayhew et al., *Biochimica et Biophysica Acta*, Vol 755, pp. 169-74 (1984); Cheng et al, *Investigative Radiology*, Vol. 22, pp. 47-55 (1987); PCT/US89/05040, U.S. Pat. No. 4,162,282; U.S. Pat. No. 4,310,505; U.S. Pat. No. 4,921,706; and *Liposome Technology*, Gregoriadis, G., ed., Vol. I, pp. 29-37, 51-67 and 79-108 (CRC Press Inc., Boca Raton, Fla. 1984). The disclosures of each of the foregoing patents, publications and patent applications are incorporated by reference herein, in their entirety. Although any of a number of varying techniques can be employed, preferably the liposomes are prepared via microemulsification techniques. The liposomes produced by the various conventional procedures can then be employed in the vacuum drying gas instillation method of the present invention, to produce the liposomes of the present invention.

The materials which may be utilized in preparing liposomes to be employed in the vacuum drying gas instillation method of the present invention include any of the materials or combinations thereof known to those skilled in the art as suitable for liposome construction. The lipids used may be of either natural or synthetic origin. Such materials include, but are not limited to, lipids such as fatty acids, lysolipids, dipalmitoylphosphatidylcholine, phosphatidylcholine, phosphatidic acid, sphingomyelin, cholesterol, cholesterol hemisuccinate, tocopherol hemisuccinate, phosphatidylethanolamine, phosphatidylinositol, lysolipids, sphingomyelin, glycosphingolipids, glucolipids, glycolipids, sulphatides, lipids with ether and ester-linked fatty acids, polymerized lipids, diacetyl phosphate, stearylamine, distearoylphosphatidylcholine, phosphatidylserine, sphingomyelin, cardiolipin, phospholipids with short chain fatty acids of 6-8 carbons in length, synthetic phospholipids with asymmetric acyl chains (e.g., with one acyl chain of 6 carbons and another acyl chain of 12 carbons), 6-(5-cholesten-3$\beta$-yloxy)-1-thio-$\beta$-D-galactopyranoside, digalactosyldiglyceride, 6-(5-cholesten-3$\beta$-yloxy)hexyl-6-amino-6-deoxy-1-thio-$\beta$-D-galactopyranoside, 6-(5-cholesten-3$\beta$-yloxy)hexyl-6-amino-6-deoxyl-1-thio-$\alpha$-D-mannopyranoside, dibehenoylphosphatidylcholine, dimyristoylphosphatidylcholine, dilauroylphosphatidylcholine, and dioleoylphosphatidylcholine, and/or combinations thereof. Other useful lipids or combinations thereof apparent to those skilled in the art which are in keeping with the spirit of the present invention are also encompassed by the present invention. For example, carbohydrate bearing lipids may be employed for in vivo targeting, as described in U.S. Pat. No. 4,310,505. Of particular interest for use in the present invention are lipids which are in the gel state (as compared with the liquid crystalline state) at the temperature at which the vacuum drying gas instillation is performed. The phase transition temperatures of various lipids will be readily apparent to those skilled in the art and are described, for example, in *Liposome Technol-* ogy, Gregoriadis, G., ed., Vol. I, pp. 1–18 (CRC Press, Inc. Boca Raton, Fla. 1984), the disclosures of which are incorporated herein by reference in their entirety. In addition, it has been found that the incorporation of at least a small amount of negatively charged lipid into any liposome membrane, although not required, is beneficial to providing highly stable liposomes. By at least a small amount, it is meant about 1 mole percent of the total lipid. Suitable negatively charged lipids will be readily apparent to those skilled in the art, and include, for example phosphatidylserine and fatty acids. Most preferred for the combined reasons of ultimate hyperthermia potentiation, ecogenicity, and stability following the vacuum drying gas instillation process are liposomes prepared from dipalmitoylphosphatidylcholine.

By way of general guidance, dipalmitoylphosphatidylcholine liposomes may be prepared by suspending dipalmitoylphosphatidylcholine lipids in phosphate buffered saline or water, and heating the lipids to about 50° C., a temperature which is slightly above the 45° C. temperature required for transition of the dipalmitoylphosphatidylcholine lipids from a gel state to a liquid crystalline state, to form liposomes. To prepare multilamellar vesicles of a rather heterogeneous size distribution of around 2 microns, the liposomes may then be mixed gently by hand while keeping the liposome solution at a temperature of about 50° C. The temperature is then lowered to room temperature, and the liposomes remain intact. Extrusion of dipalmitoylphosphatidylcholine liposomes through polycarbonate filters of defined size may, if desired, be employed to make liposomes of a more homogeneous size distribution. A device useful for this technique is an extruder device (Extruder Device TM, Lipex Biomembranes, Vancouver, Canada) equipped with a thermal barrel so that extrusion may be conveniently accomplished above the gel state-liquid crystalline transition temperature for lipids.

Alternatively, and again by way of general guidance, conventional freeze-thaw procedures may be used to produce either oligolamellar or unilamellar dipalmitoylphosphatidylcholine liposomes. After the freeze-thaw procedures, extrusion procedures as described above may then be performed on the liposomes.

The liposomes thus prepared may then be subjected to the vacuum drying gas instillation process of the present invention, to produce the vacuum dried gas instilled liposomes, and the gas filled liposomes substantially devoid of liquid in the interior thereof, of the invention. In accordance with the process of the invention, the liposomes are placed into a vessel suitable for subjecting to the liposomes to negative pressure (that is, reduced pressure or vacuum conditions). Negative pressure is then applied for a time sufficient to remove substantially all liquid from the liposomes, thereby resulting in substantially dried liposomes. As those skilled in the art would recognize, once armed with the present disclosure, various negative pressures can be employed, the important parameter being that substantially all of the liquid has been removed from the liposomes. Generally, a negative pressure of at least about 700 mm Hg, and preferably in the range of between about 700 mm Hg and about 760 mm Hg (gauge pressure) applied for about 24 to about 72 hours, is sufficient to remove substantially all of the liquid from the liposomes. Other suitable pressures and time periods will be apparent to those skilled in the art, in view of the disclosures herein.

Finally, a selected gas is applied to the liposomes to instill the liposomes with gas until ambient pressures are achieved, thereby resulting in the vacuum dried gas instilled liposomes of the invention, and in the gas filled liposomes substantially devoid of liquid in the interior thereof. Preferably, gas instillation occurs slowly, that is, over a time period of at least about 4 hours, most preferably over a time period of between about 4 and about 8 hours. Various biocompatible gases may be employed. Such gases include air, nitrogen, carbon dioxide, oxygen, argon, xenon, neon, helium, or any and all combinations thereof. Other suitable gases will be apparent to those skilled in the art, the gas chosen being only limited by the proposed application of the liposomes.

The above described method for production of liposomes is referred to hereinafter as the vacuum drying gas instillation process.

If desired, the liposomes may be cooled, prior to subjecting the liposomes to negative pressure, and such cooling is preferred. Preferably, the liposomes are cooled to below 0° C., more preferably to between about −10° C. and about −20° C., and most preferably to −10° C., prior to subjecting the liposomes to negative pressure. Upon reaching the desired negative pressure, the liposomes temperature is then preferably increased to above 0° C., more preferably to between about 10° C. and about 20° C., and most preferably to 10° C., until substantially all of the liquid has been removed from the liposomes and the negative pressure is discontinued, at which time the temperature is then permitted to return to room temperature.

If the liposomes are cooled to a temperature below 0° C., it is preferable that the vacuum drying gas instillation process be carried out with liposomes either initially prepared in the presence of cryoprotectants, or liposomes to which cryoprotectants have been added prior to carrying out the vacuum drying gas instillation process of the invention. Such cryoprotectants, while not mandatorily added, assist in maintaining the integrity of liposome membranes at low temperatures and also add to the ultimate stability of the membranes. Preferred cryoprotectants are trehalose, glycerol, polyethyleneglycol (especially polyethyleneglycol of molecular weight 400), raffinose, sucrose, and sorbitol, with trehalose being particularly preferred.

It has also been surprisingly discovered that the liposomes of the invention are highly stable to changes in pressure. Because of this characteristic, extrusion of the liposomes through filters of defined pore size following vacuum drying and gas instillation can be carried out, if desired, to create liposomes of relatively homogeneous and defined pore size.

For storage prior to use, the liposomes of the present invention may be suspended in an aqueous solution, such as a saline solution (for example, a phosphate buffered saline solution), or simply water, and stored preferably at a temperature of between about 2° C. and about 10° C., preferably at about 4° C. Preferably, the water is sterile. Most preferably, the liposomes are stored in a hypertonic saline solution (e.g., about 0.3 to about 0.5% NaCl), although if desired, the saline solution may be isotonic. The solution also may be buffered, if desired, to provide a pH range of pH 6.8 to pH 7.4. Suitable buffers include, but are not limited to, acetate, citrate, phosphate and bicarbonate. Dextrose may also be included in the suspending media. Preferably, the aqueous solution is degassed (that is, degassed under vacuum pressure) prior to suspending the liposomes therein. Bacteriostatic agents may also be included with the liposomes to prevent bacterial degradation on storage. Suitable bacteriostatic agents include but are not limited to benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid. One or more antioxidants may further be included with the gas filled liposomes to prevent oxidation of the lipid. Suitable antioxidants include tocopherol, ascorbic acid and ascorbyl palmitate. Liposomes prepared in the various foregoing manners may be stored for at least several weeks or months. Liposomes of the present invention may alternatively, if desired, be stored in their dried, unsuspended form, and such liposomes also have a shelf life of greater than several weeks or months. Specifically, the liposomes of the present invention, stored either way, generally have a shelf life stability of greater than about three weeks, preferably a shelf life stability of greater than about four weeks, more preferably a shelf life stability of greater than about five weeks, even more preferably a shelf life stability of greater than about three months, and often a shelf life stability that is even much longer, such as over six months, twelve months or even two years.

As another aspect of the invention, useful apparatus for preparing the vacuum dried gas instilled liposomes, and the gas filled liposomes substantially devoid of liquid in the interior thereof, of the invention is also presented. Specifically, there is shown in FIG. 1 a preferred apparatus for vacuum drying liposomes and instilling a gas into the dried liposomes. The apparatus is comprised of a vessel 8 for containing liposomes 19. If desired, the apparatus may include an ice bath 5 containing dry ice 17 surrounding the vessel 8. The ice bath 5 and dry ice 17 allow the liposomes to be cooled to below 0° C. A vacuum pump 1 is connected to the vessel 8 via a conduit 15 for applying a sustained negative pressure to the vessel. In the preferred embodiment, the pump 1 is capable of applying a negative pressure of at least 700 mm Hg and preferably a negative pressure in the range of about 700 mm Hg to about 760 mm Hg (gauge pressure). A manometer 6 is connected to the conduit 15 to allow monitoring of the negative pressure applied to the vessel 8.

In order to prevent liquid removed from the liposomes from entering the pump 1, a series of traps are connected to the conduit 15 to assist in collecting the liquid (and liquid vapor, all collectively referred to herein as liquid) drawn from the liposomes. In a preferred embodiment, two traps are utilized. The first trap is preferably comprised of a flask 7 disposed in an ice bath 4 with dry ice 17. The second trap is preferably comprised of a column 3 around which tubing 16 is helically arranged. The column 3 is connected to the conduit 15 at its top end and to one end of the tubing 16 at its bottom end. The other end of the tubing 16 is connected to the conduit 15. As shown in FIG. 1, an ice bath 2 with dry ice 17 surrounds the column 3 and tubing 16. If desired, dry ice 17 can be replaced with liquid nitrogen, liquid air or other cryogenic material. The ice baths 2 and 4 assist in collecting any liquid and condensing any liquid vapor drawn from the liposomes for collection in the traps. In preferred embodiments of the present invention the ice traps 2 and 4 are each maintained at a temperature of least about −70° C.

A stopcock 14 is disposed in the conduit 15 upstream of the vessel 8 to allow a selected gas to be introduced into the vessel 8 and into liposomes 19 from gas bottle 18.

Apparatus of the present invention are utilized by placing the liposomes 19 into vessel 8. In a preferable embodiment, ice bath 5 with dry ice 17 is used to lower the temperature of the liposomes to below 0° C., more preferably to between about −10° C. and about −20° C., and most preferably to −10° C. With stopcocks 14 and 9 closed, vacuum pump 1 is turned on. Stopcocks 10, 11, 12 and 13 are then carefully opened to create a vacuum in vessel 8 by means of vacuum pump 1. The pressure is gauged by means of manometer 6 until negative pressure of at least 700 mm Hg and preferably in the range of between about 700 mm Hg and about 760 mm Hg, is achieved. In preferred embodiments of the present invention, vessel 7, cooled by ice bath 4 with dry ice 17, and column 3 and coil 16, cooled by ice bath 2 with dry ice 17, together or individually condense liquid vapor and trap liquid drawn from the liposomes so as to prevent such liquids and liquid vapor from entering the vacuum pump 1. In preferred embodiments of the present invention, the temperature of ice traps 2 and 4 are each maintained at a temperature of at least about −70° C. The desired negative pressure is generally maintained for at least 24 hours as liquid and liquid vapor is removed from the liposomes 19 in vessel 8 and frozen in vessels 3 and 7. Pressure within the system is monitored using manometer 6 and is generally maintained for about 24 to about 72 hours, at which time substantially all of the liquid has been removed from the liposomes. At this point, stopcock 10 is slowly closed and vacuum pump 1 is turned off. Stopcock 14 is then opened gradually and gas is slowly introduced into the system from gas bottle 18 through stopcock 14 via conduit 15 to instill gas into the liposomes 19 in vessel 8. Preferably, the gas instillation occurs slowly over a time period of at least about 4 hours, most preferably over a time period of between about 4 and about 8 hours, until the system reaches ambient pressure.

The vacuum dried gas instilled liposomes and the gas filled liposomes substantially devoid of liquid in the interior thereof of the present invention have superior characteristics for use as hyperthermia potentiators. The subject liposomes provide good heating of surrounding tissues and/or fluids on ultrasound, are highly stable to pressure, and/or generally possess a long storage life either when stored dry or suspended in a liquid medium. In use, the hyperthermic potentiators of the present invention are administered to a biological tissue or to biological fluids, whereupon ultrasound is then applied to the biological matter. The methods of the invention are particularly useful when employed in relation to such biological matter as tumor tissue, muscle tissue or blood fluid.

The liposomes employed may be of varying sizes, but preferably are of a size range wherein they have a mean outside diameter between about 30 nanometers and about 10 microns, with the preferable mean outside diameter being about 2 microns. As is known to those skilled in the art, liposome size influences biodistribution and, therefore, different size liposomes are selected for various purposes. For intravascular use, for example, liposome size is generally no larger than about 5 microns, and generally no smaller than about 30 nanometers, in mean outside diameter. For non-vascular uses, larger liposomes, e.g., between about 2 and about 10 micron mean outside diameter may be employed, if desired.

The lipids employed may be selected to optimize the particular therapeutic use, minimize toxicity and maximize shelf-life of the product. Neutral liposomes composed of either saturated or unsaturated phosphatidylcholine, with or without sterol, such as cholesterol, function quite well as intravascular hyperthermia potentiators entrapping gas. To improve uptake by cells such as the reticuloendothelial system (RES), a negatively charged lipid such as phosphatidylglycerol, phosphatidylserine or similar materials is added. For even greater liposome stability, the liposome can be polymerized using polymerizable lipids, or the surface of the liposome can be coated with polymers such as polyethylene glycol so as to protect the surface of the vesicle from serum proteins, or gangliosides such as GM1 can be incorporated within the lipid matrix. Liposomes may also be prepared with attached receptors or antibodies to facilitate their targeting to specific cell types such as tumors. Most preferred for reasons of their hyperthermia potentiation and stability are liposomes prepared from dipalmitoylphosphatidyl choline.

Where the usage is in vivo, administration may be carried out in various fashions, such as intravascularly, intralymphatically, parenterally, subcutaneously, intramuscularly, intraperitoneally, interstitially, hyperbarically, orally, or intratumorly using a variety of dosage forms, the particular route of administration and the dosage used being dependent upon the type of therapeutic use sought, and the particular potentiating agent employed. For example, in tumors with a principal dominant arterial supply such as the kidney, these hyperthermic potentiating agents may be administered intraarterially. Typically, dosage is initiated at lower levels and increased until the desired temperature increase effect is achieved. Generally, the contrast agents of the invention are administered in the form of an aqueous suspension such as in water or a saline solution (e.g., phosphate buffered saline). Preferably, the water is sterile. Also preferably the saline solution is a hypertonic saline solution (e.g., about 0.3 to about 0.5% NaCl), although, if desired, the saline solution may be isotonic. The solution also may be buffered, if desired, to provide a pH range of pH 6.8 to pH 7.4. In addition, dextrose may be preferably included in the media. Preferably, the aqueous solution is degassed (that is, degassed under vacuum pressure) prior to suspending the liposomes therein.

For in vivo usage, the patient can be any type of mammal, but most preferably is a human. The method of the invention is particularly useful in the treatment of tumors, various inflammatory conditions, and arthritis, especially in the treatment of tumors. The gas filled liposomes prepared by a vacuum drying gas instillation method and the gas filled liposomes substantially devoid of liquid in the interior thereof accumulate in tumors, particularly in the brain, because of the leaky capillaries and delayed wash-out from the diseased tissues. Similarly, in other regions of the body where tumor vessels are leaky, the hyperthermic potentiating agents will accumulate.

The hyperthermic potentiators of the present invention may be used alone, in combination with one another, or in combination with other therapeutic and/or diagnostic agents. In tumor therapy applications, for example, the hyperthermic potentiators may be administered in combination with various chemotherapeutic agents.

Any of the various types of ultrasound imaging devices can be employed in the practice of the invention, the particular type or model of the device not being critical to the method of the invention. Preferably, however, devices specially designed for administering ultrasonic hyperthermia are preferred. Such devices are described U.S. Pat. Nos. 4,620,546, 4,658,828, and 4,586,512, the disclosures of each of which are hereby incorporated herein by reference in their entirety. The use of a device designed for administering ultrasonic hyperthermia and incorporating resonant frequency (RF) spectral analyzer is particularly preferred.

Although applicant does not intend to be limited to any particular theory of operation, the hyperthermic potentiators employed in the methods of the present invention are believed to possess their excellent results because of the following scientific postulates.

Ultrasonic energy may either be transmitted through a tissue, reflected or absorbed. It is believed that the potentiators of the invention serve to increase the absorption of sound energy within the biological tissues or fluids in which they are present, which results in increased heating, thereby increasing the therapeutic effectiveness of ultrasonic hyperthermia.

Absorption of sound is believed to be increased in acoustic regions which have a high degree of ultrasonic heterogeneity. Soft tissues and fluids with a higher degree of heterogeneity will absorb sound at a higher rate than tissues or fluids which are more homogeneous acoustically. When sound encounters an interface which has a different acoustic impedance than the surrounding medium, there is believed to be both increased reflection of sound and increased absorption of sound. The degree of absorption of sound is believed to rise as the difference between the acoustic impedances between the two substances comprising the interface increases. The potentiators of the present invention provide high acoustic impedance differences between the potentiators and any surrounding liquids and tissues.

Intense sonic energy is also believed to cause cavitation and, when cavitation occurs, this in turn is thought to cause intense local heating. Gas bubbles are believed to lower the cavitation threshold, that is, accelerate the process of cavitation during sonication.

Since the potentiators of the present invention provide high acoustic impedance differences between the potentiators and the surrounding liquids and tissues, as well as decrease the cavitation threshold, the subject potentiators may act to increase the rate of absorption of ultrasonic energy in the surrounding tissues and fluids and effect a conversion of that energy into local heat. Additionally, the low thermal conductivity of gas may serve to decrease local heat dissipation, with the result that there is both an increase in the rate of heating and an increase in the final equilibrium temperature.

The potentiators of the present invention may serve to increase the acoustic heterogeneity and generate cavitation nuclei in tumors and tissues thereby acting as a potentiator of heating in ultrasonic hyperthermia. Because the gas creates an acoustic impedance mismatch with adjacent tissues and adjacent fluids, the gas acts to increase the absorption of sound and conversion of the energy into heat in the surrounding tissues and fluids.

The liposomes of the present invention are believed to differ from the liposomes of the prior art in a number of respects, both in physical and in functional characteristics. For example, the liposomes of the invention are substantially devoid of liquid in the interior thereof. By definition, liposomes in the prior art have been characterized by the presence of an aqueous medium. See, e.g., *Dorland's Illustrated Medical Dictionary*, p. 946, 27th ed. (W. B. Saunders Company, Philadelphia 1988). Moreover, the present liposomes surprisingly result in good heating of surrounding tissues and/or fluids on ultrasound, and posses a long storage life, characteristics of obvious importance to the hyperthermic potentiator applications of the invention.

There are various other applications for liposomes of the invention beyond those described in detail herein. Such additional uses, for example, include such application as drug delivery vehicles and as contrast agents for ultrasonic imaging. Such additional uses and other related subject matter are described and claimed in Applicant's patent applications filed concurrently herewith entitled "Novel Liposomal Drug Delivery Systems" and "Gas Filled Liposomes And Their Use As Ultrasonic Contrast Agents", the disclosures of each of which are incorporated herein by reference in their entirety.

The following examples are merely illustrative of the present invention and should not be considered as limiting the scope of the invention in any way. These examples and equivalents thereof will become more apparent to those versed in the art in light of the present disclosure, and the accompanying claims.

Examples 1-8 are actual examples that describe the preparation and testing of the vacuum dried gas instilled liposomes, the gas filled liposomes being substantially devoid of any liquid in the interior thereof, of the invention. Examples 9-13 are prophetic examples meant to be illustrative of how the invention would operate under the specified conditions.

EXAMPLES

Example 1

Dipalmitoylphosphatidylcholine (1 gram) was suspended in 10 ml phosphate buffered saline, the suspension was heated to about 50° C., and then swirled by hand in a round bottom flask for about 30 minutes. The heat source was removed, and the suspension was swirled for two additional hours, while allowing the suspension to cool to room temperature, to form liposomes.

The liposomes thus prepared were placed in a vessel in an apparatus similar to that shown in FIG. 1 cooled to about −10° C., and then subjected to high negative vacuum pressure. The temperature of the liposomes was then raised to about 10° C. High negative vacuum pressure was maintained for about 48 hours. After about 48 hours, nitrogen gas was gradually instilled into the chamber over a period of about 4 hours, after which time the pressure returned to ambient pressure. The resulting vacuum dried gas instilled liposomes, the gas filled liposomes being substantially devoid of any liquid in the interior thereof, were then suspended in 10 cc of phosphate buffered saline and stored at about 4° C. for about three months.

Example 2

Figure 2:
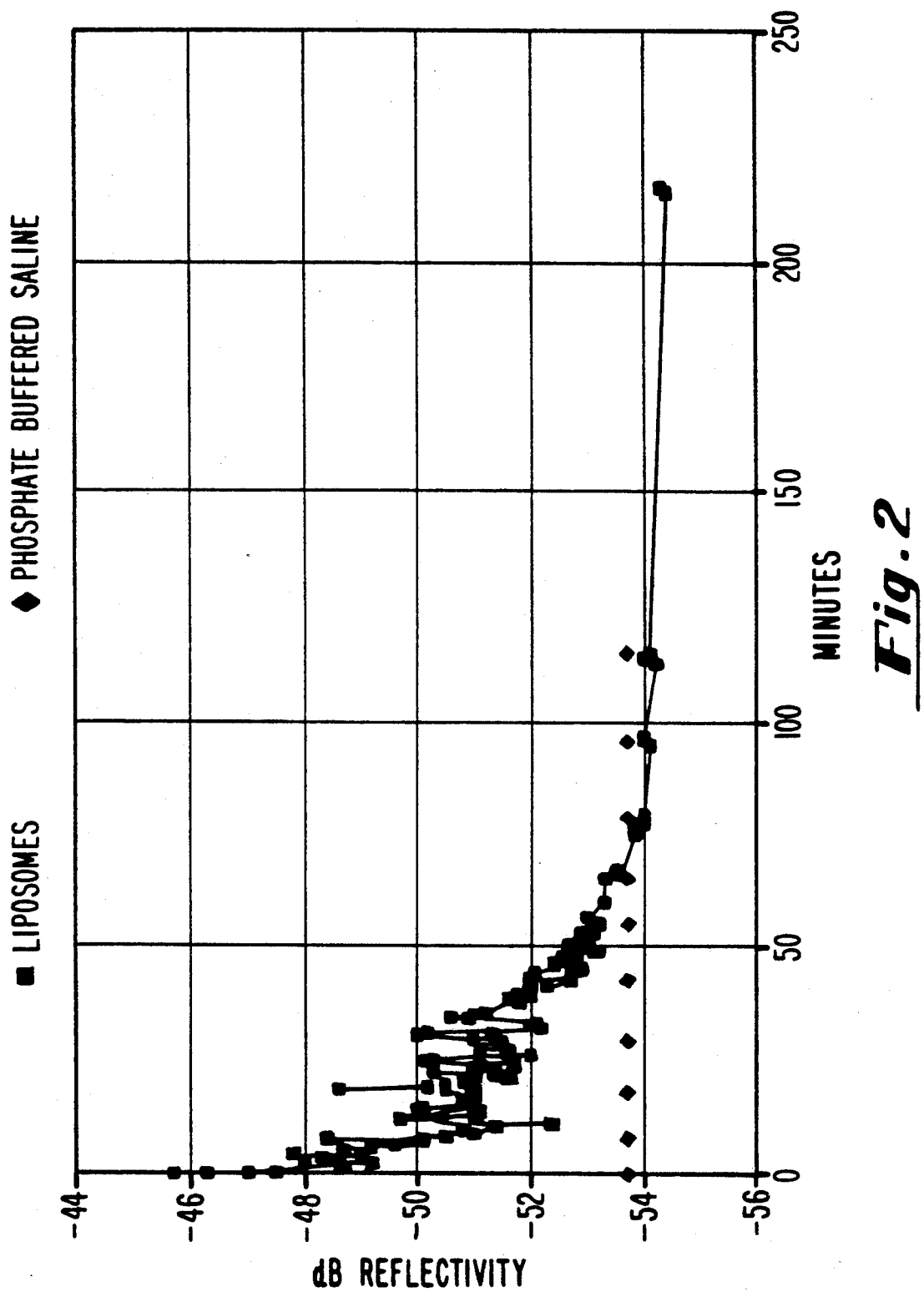
FIG. 2 is a graphical representation of the dB reflectivity of the vacuum dried gas instilled liposomes and the gas filled liposomes substantially devoid of liquid in the interior thereof prepared by the vacuum drying gas instillation method. The data was obtained by scanning with a 7.5 megahertz transducer using an Acoustic Imaging ™ Model 5200 Scanner (Acoustic Imaging, Phoenix, Ariz.), and was generated using the system test software to measure reflectivity. The system was standardized prior to each experiment with a phantom of known acoustic impedance.

To test the liposomes of Example 1 ultrasonographically, a 250 mg sample of these liposomes was suspended in 300 cc of degassed phosphate buffered saline (that is, degassed under vacuum pressure). The liposomes were then scanned in vitro at varying time intervals with a 7.5 mHz transducer using an Acoustic Imaging Model 5200 scanner (Acoustic Imaging, Phoenix, Ariz.) and employing the system test software to measure dB reflectivity. The system was standardized prior to testing the liposomes with a phantom of known acoustic impedance. A graph showing dB reflectivity is provided in FIG. 2.

Example 3

Dipalmitoylphosphatidylcholine (1 gram) and the cryoprotectant trehalose (1 gram) were suspended in 10 ml phosphate buffered saline, the suspension was heated to about 50° C., and then swirled by hand in a round bottom flask for about 30 minutes. The heat source was removed, and the suspension was swirled for about two additional hours, while allowing the suspension to cool to room temperature, to form liposomes.

The liposomes thus prepared were then vacuum dried and gas instilled, substantially following the procedures shown in Example 1, resulting in vacuum dried gas instilled liposomes, the gas filled liposomes being substantially devoid of any liquid in the interior thereof. The liposomes were then suspended in 10 cc of phosphate buffered saline, and then stored at about 4° C. for several weeks.

Example 4

To test the liposomes of Example 3 ultrasonographically, the procedures of Example 2 were substantially followed. The dB reflectivity of the liposomes were similar to the dB reflectivity reported in Example 2.

Example 5

Dipalmitoylphosphatidylcholine (1 gram) was suspended in 10 ml phosphate buffered saline, the suspension was heated to about 50° C., and then swirled by hand in a round bottom flask for about 30 minutes. The suspension was then subjected to 5 cycles of extrusion through an extruder device jacketed with a thermal barrel (Extruder Device TM, Lipex Biomembranes, Vancouver, Canada), both with and without conventional freeze-thaw treatment prior to extrusion, while maintaining the temperature at about 50° C. The heat source was removed, and the suspension was swirled for about two additional hours, while allowing the suspension to cool to room temperature, to form liposomes.

The liposomes thus prepared were then vacuum dried and gas instilled, substantially following the procedures shown in Example 1, resulting in vacuum dried gas instilled liposomes, the gas filled liposomes being substantially devoid of any liquid in the interior thereof. The liposomes were then suspended in 10 cc of phosphate buffered saline, and then stored at about 4° C. for several weeks.

Example 6

To test the liposomes of Example 5 ultrasonographically, the procedures of Example 2 were substantially followed. The dB reflectivity of the liposomes were similar to the dB reflectivity reported in Example 2.

Example 7

In order to test the stability of the liposomes of the invention, the liposomes suspension of Example 1 was passed through 2 micron polycarbonate filters in an extruder device (Extruder Device TM, Lipex Biomembranes, Vancouver, Canada) five times at a pressure of about 600 psi. After extrusion treatment, the liposomes were studied ultrasonographically, as described in Example 2. Surprisingly, even after extrusion under high pressure, the liposomes of the invention substantially retained their echogenicity.

Example 8

The liposomes of Example 1 were scanned by ultrasound using transducer frequencies varying from 3 to 7.5 mHz. The results indicated that at a higher frequency of ultrasound, the echogenicity decays more rapidly, reflecting a relatively high resonant frequency and higher energy associated with the higher frequencies.

The following examples, Examples 9-13, are prophetic examples.

Example 9

A patient with cancer is administered a dose of gas filled liposomes prepared by a vacuum drying gas instillation method, the liposomes being substantially devoid of liquid in the interior thereof. Accumulation of the liposomes in the tumor is verified ultrasonigraphically. Focused ultrasonic hyperthermia is then administered to the tumor and the liposomes therein. The tumor has an increased rate of heating compared to treatment using ultrasonic hyperthermia without the liposomes.

Example 10

An ultrasonic device designed for administering ultrasonic hyperthermia and incorporating an RF spectral analyzer was employed. After gas filled liposomes prepared by a vacuum drying gas instillation method, the liposomes being substantially devoid of liquid in the interior thereof, are delivered intravenously, the RF signal in a lesion in the patient is monitored by the ultrasonic hyperthermia RF spectral analyzer. Even though the concentration of gas filled liposomes may be too dilute to visualize on an image ultrasonographically, the RF spectral analyzer detects a change in the peak of the RF spectrum. The peak in the RF spectrum reflects the harmonic frequency of the gas filled liposomes. This data enables the operator to the ultrasonic hyperthermia equipment to adjust the application of the ultrasonic energy to coincide with the maximal intra-lesional concentration of the gas filled liposomes and to evaluate the disappearance of the gas filled liposomes as hyperthermia progresses. Assessment of the resonant frequency also allows the operator to adjust the frequency, amplitude, duration and pulse repetition rate to be maximally effective at heating the tumor through the augmenting effects of the bubbles. Further, the presence of the gas filled liposomes in the lesion allows the operator to assess the blood flow through the diseased tissues, information of great value in determining the rate of washout of heat from the tumor. Information regarding blood flow can be obtained either from simple subjective assessment of the images under real time ultrasound or by quantitative assessment through integration of the peaks in the RF spectrums reflecting the resonant frequencies of the gas filled liposomes.

Example 11

Gas filled liposomes prepared by a vacuum drying gas instillation method, the liposomes being substantially devoid of liquid in the interior thereof and entrapping oxygen gas, are administered intravenously to a patient with cancer. Ultrasonic hyperthermia is performed with pulses of high energy ultrasound and cavitation occurs at the sites of the bubbles. The oxygen increases the rate of formation of free radicals which help to destroy the tumor tissue.

Example 12

In a patient with cancer, gas filled liposomes prepared by a vacuum drying gas instillation method, the liposomes being substantially devoid of liquid in the interior thereof and entrapping oxygen, are administered intravenously and the patient is then scanned via ultrasound. When the peak concentration of liposomes is in the tumor, the tumor is simultaneously treated with hyperthermia and radiation therapy. The effect of the liposomes and hyperthermia magnifies the effectiveness of the radiation therapy by releasing oxygen to form free radicals generated by the ionizing radiation and also formed by cavitation to improve the response of the tumor to combined radiation and hyperthermia.

Various modifications in addition to those shown and described herein will be apparent to those skilled in the art from the foregoing description. Such modifications are also intended to fall within the scope of the appended claims.

Example 13

Gas filled liposomes prepared by a vacuum drying gas instillation method, the liposomes being substantially devoid of liquid in the interior thereof and entrapping argon gas, are administered intravenously to a patient with cancer. Ultrasonic hyperthermia is performed with pulses of high energy ultrasound and cavitation occurs at the sites of the bubbles. The argon increases the rate of formation of free radicals which help to destroy the tumor tissue.

What is claimed is:

1. A method for heat treating biological tissues and fluids which comprises:
   (i) administering to the tissue or fluid to be treated a therapeutically effective amount of a hyperthermia potentiator comprising gas filled liposomes prepared by a vacuum drying gas instillation method; and
   (ii) applying ultrasound to said tissue or fluid.

2. A method of claim 1 wherein said liposomes are comprised of lipid materials selected from the group consisting of fatty acids, lysolipids, dipalmitoylphosphatidylcholine, phosphatidylcholine, phosphatidic acid, sphingomyelin, cholesterol, cholesterol hemisuccinate, tocopherol hemisuccinate, phosphatidylethanolamine, phosphatidylinositol, lysolipids, sphingomyelin, glycosphingolipids, glucolipids, glycolipids, sulphatides, lipids with ether and ester-linked fatty acids, and polymerized lipids.

3. A method of claim 2 wherein said liposomes are comprised of dipalmitoylphosphatidylcholine.

4. A method of claim 1 wherein said liposomes are filled with a gas selected from the group consisting of air, nitrogen, carbon dioxide, oxygen, argon, xenon, helium, and neon.

5. A method of claim 4 wherein said liposomes are filled with nitrogen gas.

6. A method of claim 1 wherein said liposomes are suspended in an aqueous medium.

7. A method of claim 6 wherein said aqueous medium is phosphate buffered saline.

8. A method of claim 1 wherein said liposomes are administered to tissue or fluid selected from the group consisting of tumor tissue, muscle tissue, and blood fluid.

9. A method for heat treating biological tissues and fluids which comprises:
   (i) administering to the tissue or fluid to be treated a therapeutically effective amount of a hyperthermia potentiator comprising gas filled liposomes substantially devoid of liquid in the interior thereof; and
   (ii) applying ultrasound to said tissue or fluid.

10. A method of claim 9 wherein said liposomes are comprised of lipid materials selected from the group consisting of fatty acids, lysolipids, dipalmitoylphosphatidylcholine, phosphatidylcholine, phosphatidic acid, sphingomyelin, cholesterol, cholesterol hemisuccinate, tocopherol hemisuccinate, phosphatidylethanolamine, phosphatidylinositol, lysolipids, sphingomyelin, glycosphingolipids, glucolipids, glycolipids, sulphatides, lipids with ether and ester-linked fatty acids, and polymerized lipids.

11. A method of claim 10 wherein said liposomes are comprised of dipalmitoylphosphatidylcholine.

12. A method of claim 9 wherein said liposomes are filled with a gas selected from the group consisting of air, nitrogen, carbon dioxide, oxygen, argon, xenon, helium, and neon.

13. A method of claim 12 wherein said liposomes are filled with nitrogen gas.

14. A method of claim 9 wherein said liposomes are suspended in an aqueous medium.

15. A method of claim 14 wherein said aqueous medium is phosphate buffered saline.

16. A method of claim 9 wherein said liposomes are administered to tissue or fluid selected from the group consisting of tumor tissue, muscle tissue, and blood fluid.

* * * * *